(12) United States Patent
Weber et al.

(10) Patent No.: US 7,403,830 B2
(45) Date of Patent: Jul. 22, 2008

(54) METHOD, COMPUTER, COMPUTER PROGRAM AND COMPUTER-READABLE MEDIUM RELATING TO THE EXAMINATION OF DATA RECORDS FOR DENTAL PROSTHESIS PARTS

(75) Inventors: Gerhard Weber, Inning/Ammersee (DE); Stephan Holzner, Mühldorf/Inn (DE)

(73) Assignee: Willytec GmbH, Graefelfing (DE)

( * ) Notice: Subject to any disclaimer, the term of this patent is extended or adjusted under 35 U.S.C. 154(b) by 0 days.

(21) Appl. No.: 11/400,044

(22) Filed: Apr. 7, 2006

(65) Prior Publication Data
US 2006/0253215 A1  Nov. 9, 2006

(30) Foreign Application Priority Data
Apr. 8, 2005  (DE) .................. 10 2005 016 245

(51) Int. Cl.
*A61C 19/04* (2006.01)
*G06F 19/00* (2006.01)
*G05B 9/05* (2006.01)
(52) U.S. Cl. .................... 700/98; 700/97; 700/99; 700/118; 433/225; 264/16; 264/138; 264/219
(58) Field of Classification Search .............. 700/97, 700/98, 118, 99; 433/225; 264/16, 138, 264/219
See application file for complete search history.

(56) References Cited

U.S. PATENT DOCUMENTS

| 6,295,513 | B1 * | 9/2001 | Thackston ............... 703/1 |
| 6,669,875 | B2 * | 12/2003 | Meyertholen et al. ......... 264/16 |
| 2002/0137002 | A1 * | 9/2002 | Bodenmiller .............. 433/51 |
| 2003/0164952 | A1 * | 9/2003 | Deichmann et al. ........ 356/603 |
| 2003/0207235 | A1 * | 11/2003 | der Zel ................ 433/223 |
| 2004/0009376 | A1 * | 1/2004 | Wan et al. ............... 428/698 |
| 2004/0220691 | A1 * | 11/2004 | Hofmeister et al. .......... 700/98 |
| 2006/0253215 | A1 * | 11/2006 | Weber et al. ............ 700/98 |

OTHER PUBLICATIONS

"A Design Interface for 3D manufacturing" and "A Manufacturing Interface for 3D design" -Prinz et al, Stanford University, Aug. 1998.*
"Digital denture manufacturing—An integrated technologies of abrasive computer tomography, CNC machining and rapid prototyping"; Chang et al, Int. J Adv. Manuf. Technol (2006) 31: 41-49, Apr. 2006.*
"An Autonomous Smart Dental Prosthesis for Fast Rehabilitation" -Ham et al, KULeuven Dep. Electrical Engineering, IEEE 2006.*

* cited by examiner

*Primary Examiner*—Michael D. Masinick
(74) *Attorney, Agent, or Firm*—IP Strategies

(57) ABSTRACT

The invention refers to a method, a computer, a computer program and a computer-readable medium, which refer to the examination of data records that are used for manufacturing dental prosthesis parts. The examination may be the producibility by one or several methods, the mountability onto the associated residual tooth portion or the examination as to undercuts.

38 Claims, 8 Drawing Sheets

METHOD, COMPUTER, COMPUTER PROGRAM AND COMPUTER-READABLE MEDIUM RELATING TO THE EXAMINATION OF DATA RECORDS FOR DENTAL PROSTHESIS PARTS

The present invention refers to a method, a computer, a computer program and a computer-readable medium, which relate to the examination of data records that are used for manufacturing dental prosthesis parts.

Dental prosthesis parts may be bridges, inlays, overlays, crowns or the like. Dental prosthesis parts of this type are e.g. made of ceramics such as zinc oxide ceramics, aluminium oxide ceramics, in-ceram or metals or alloys such as (bio)-titanium CrCo alloys. Gold and gold alloys are also common.

In order to attach such dental prosthesis parts onto a residual tooth portion, the remaining teeth are usually ground so that a stump remains on which a dental prosthesis part can be attached. It is also known to implant implant piles into the jaw and to attach dental prosthesis parts thereon.

Dental prosthesis parts are usually fixed by using a suitable cement, adhesive or the like on the tooth residuals or implant piles. Thus, small inaccuracies of the dental prosthesis part may be compensated for. Precisely fitting dental prosthesis parts are, however, to be preferred.

To manufacture dental prosthesis parts, an impression is made from the residual tooth portion by means of which a gypsum die of the residual tooth portion is made. By scanning such a model or a residual tooth portion the shape of the residual tooth portion can be determined in the form of a data record. Starting out from such a data record or independent thereof it is known to generate data records that represent a dental prosthesis part or a part thereof. By means of such data records automatic methods of manufacturing dental prosthesis parts, such as a milling process or the like, can be used.

When grinding teeth, the implant pile or the like, it is usually attempted by manual work to grind them approximately conically to thereby enable mounting of the dental prosthesis part in a possibly simple manner. It might occasionally occur or it might be inevitable that the residual tooth portion reveals undercuts, since an assessment with the mere eye may be quite difficult in the tight oral cavity. This may lead to problems in the automatic manufacture of dental prosthesis parts.

Thus, it is the object of the invention to provide a method, a computer, a computer program and a computer-readable medium, by means of which many different kinds of dental prosthesis parts can be manufactured as cost-effective as possible.

This object is solved by a method according to claims 1, 27, 28, by a computer according to claims 29, 30 or 31, by a computer program according to claim 31, or by a computer-readable medium according to claim 32. Advantageous embodiments are disclosed in the dependent claims. Advantageous embodiments are particularly also given by a combination of the method 27 with the respective method steps of claims 11 to 26.

In a method according to claim 1, a data record is examined. The data record may exist in a computer or it may be stored therein. The data record represents a dental prosthesis part or a part thereof, such as the inner or outer side, or a part thereof and examines, whether it can be manufactured by a certain manufacturing method.

The inner side is the side of the dental prosthesis part that faces the residual tooth portion. The outer side is the side pointing away from the residual tooth portion. This side for instance includes a chewing surface.

If the dental prosthesis part that is represented by the data record for instance reveals an undercut, it is not possible to manufacture the dental prosthesis part with a 3-axis milling machine by a linear milling tool, since the area of the undercut is not accessible by the tool. This type of manufacture is, however, the most simple and cost-effective alternative. Thus, it can also be examined whether a dental prosthesis part can for instance be manufactured by a 3+1-, 4- or 5-axis milling machine, wherein the milling times on such milling machines are more expensive than those of a 3-axis milling machine.

A dental prosthesis part, which has undercuts, can still be manufactured by means of a 3-axis milling machine if a shaping tool is used. Such a tool is a milling tool, which is not cylindrical but has an outer contour that has any design so that by means of a 3-axis milling machine undercuts can be milled. However, not all types of the undercut can be manufactured by 3-axis milling machines by using such a shaping tool.

Before starting the manufacture of a dental prosthesis part, or before the machine data is calculated for a milling process or any other manufacturing process, it is therefore advantageous if it is tested whether the dental prosthesis part can be manufactured by one determined or one among several determined manufacturing methods. A dental prosthesis part that does not have any undercuts may be difficult to manufacture by a 3-axis milling machine using a normal milling tool, if the milling tool rests at a flat angle at the surface of the dental prosthesis part, since this may lead to wobbling of the tool and respective production inaccuracies. Thus, it is advantageous to take into consideration a respective limit angle between the milling tool and the surface.

It is also possible; when examining producibility, to determine and define the respective angle between the milling tool and the milled surface so that the operator of a computer, who carries out the method according to claim 1, can evaluate whether a respective manufacturing method is acceptable or not.

Advantageously, an automatic selection of a manufacturing method takes place after the producibility test. Thereby cost-optimized manufacturing methods can be preferred to cost-intensive methods. The result of a respective selection may be output advantageously in a suitable manner. Besides the costs caused by the manufacturing methods, the costs for raw materials may also be taken into consideration, which may vary depending on the manufacturing methods, since for instance blanks with different heights may be used.

In addition to examining producibility using a certain manufacturing method it is also advantageous to test the data record in advance, i.e. before manufacture of the dental prosthesis part or before generation of the machine data, whether the dental prosthesis part will be capable of being mounted onto the residual tooth part. However, it is basically also possible to test this with a manufactured dental prosthesis part. When examining whether the dental prosthesis part can be mounted onto the residual tooth portion, the data record that represents the residual tooth portion is taken into consideration.

For examining whether the dental prosthesis part can be mounted onto the residual tooth portion it is advantageous to simulate different relative positions of the two data records with respect to one another. Mounting the dental prosthesis part onto the residual tooth portion and removing the dental prosthesis part from the residual tooth portion can be simulated. It can also be simulated to pivot the dental prosthesis part into the residual tooth portion or to pivot the dental prosthesis part way from the residual tooth portion.

A method is the most simple in which the dental prosthesis part is simulated in the desired position compared to the residual tooth portion and it is subsequently examined whether the dental prosthesis part can be moved away from the residual tooth portion by linear or rotational movements. The reversed way, in which the mounting is simulated is, however, also possible.

A method is particularly advantageous in which the inherent movability of the teeth is taken into consideration. By anchoring the teeth in the jaw, an inherent movability of the teeth is given in the case of normal teeth. However, implant piles are fixedly connected to the jaw so that an inherent movability does then not exist. A dental prosthesis part, which has a small undercut, can therefore be snapped open in the case of movable teeth by utilizing the inherent movability, whereas it could not be mounted on in the case of implant piles having an identical shape. Thus, it is advantageous to identify tooth portions compared to gingival areas or implant piles, which advantageously takes place automatically by a respective shape detection or by the input of information by means of which a part of the data record is identified as a tooth, so that an inherent movability can be associated to this tooth portion. Pre-adjusted data for tooth movability can also be taken into consideration.

When examining mountability, the tooth movability can be taken into consideration and it can thereby be determined in how far the teeth must be moved to mounting or removing the dental prosthesis part. A respective information can be output so that an operator may assess whether the required dental movability is given.

If during the examination whether the dental prosthesis part can be manufactured and/or mounted the result is obtained that the dental prosthesis part cannot be manufactured by a determined manufacturing method and/or cannot be mounted, a preparation instruction is immediately generated, which indicates how the residual tooth portion is to be modified to eliminate the problems which have lead to the fact that the dental prosthesis part cannot be manufactured and/or cannot be mounted by a certain manufacturing method. The preparation instruction can advantageously be made in the form of text and/or images by an image output, a print-out or in any other manner.

It is also possible, if the manufacturing or mountability examination has a negative result, to modify the data record of the dental prosthesis part, so that a mountability and/or a producibility with one or several determined manufacturing methods is given.

The modification of the data record is advantageously carried out automatically. However, it may also be carried out manually by a respective data input which modifies the data record of the dental prosthesis part respectively. An automatic modification of the data record of the dental prosthesis part will be carried out by means of certain criteria. These may for instance be a sufficient material strength, wherein the material strength required will depend on the material of the dental prosthesis part.

It is also advantageous if in the modification a complete inclusion of the tooth stump remains or is maintained. To protect the stump of the tooth for instance from caries it is advantageous that this stump is fully enclosed by the dental prosthesis part. For this purpose the dental prosthesis part must rest on the gingival edge along the stump of the tooth possibly close to the stump of the tooth.

It is also advantageous if a possibly complete contact between the stump of the tooth and/or the implant pile or the like is obtained or is maintained, since then a possibly high adhesive effect can be achieved for the dental prosthesis part caused by the adhesive between the dental prosthesis part and the residual tooth portion.

Furthermore, the manufacturing costs, manufacturing time, possible manufacturing methods or definitions for the outer dimensions of the dental prosthesis part can be taken into consideration in the modification of the data record.

An embodiment of the method is particularly advantageous in which first of all only the inner side of the dental prosthesis part is examined. The examination may refer to the examination of undercuts, the producibility by a certain manufacturing method or the mountability on the inner side onto the associated residual tooth portion. Either only one data record of the inner side may be taken into consideration or only the part of the data record that represents the inner side.

If problems occur in the producibility or mountability, the inner side of the dental prosthesis part can, as described above, be modified.

After positive examination of the data record, which represents the inner side of the dental prosthesis part, or after a respective modification of same, the outer side is then automatically or manually shaped. The manual shaping would also be a computer-aided shaping, in which the outer side is shaped by input of data into a computer by an operator. An automatic shaping takes place without the action of an operator. Various criteria can be taken into consideration when shaping the outer side, such as the wall thickness of the dental prosthesis part, the material of the dental prosthesis part, manufacturing costs, duration, the possible manufacturing methods and the possibly predefined maximum outer dimensions.

In a preferred embodiment, parameters referring to the milling process and thus also to the milling accuracy are set by means of the data record of the dental prosthesis part. These parameters may for instance be the infeed speed of the milling head, the speed of the milling tool, the type of milling tool, the use or the type of coolant to be used. Those areas that need an increased accuracy may for instance be milled at a low infeed speed, whereas less critical areas can be milled faster. The same applies to the other milling parameters. The outer side of a dental prosthesis part does not need such a high precision compared to the inner side. The area of the preparation boundary must be manufactured particularly precisely, i.e. the portion that is located at the edge of the contact between the dental prosthesis part and the residual tooth portion, since in this case a favourable sealing between stumps and dental prosthesis part shall be given. The parameters generated are preferably stored in a *.slt file (file in stereolithography format) for the production or they are output in any other manner for being available for the milling process.

Advantageously, the required height of a blank is determined which is required for manufacturing the dental prosthesis part. Depending on the orientation of the data record with respect to the system of coordinates of a blank from which the dental prosthesis part shall be milled out, different heights of the blank are required. For minimal raw material costs, a minimal blank height is advantageous. On the other hand, an orientation of the data record may also be advantageous in which the blank height is not minimal but slightly higher, since thereby the data record can be arranged such that it is free from undercuts for milling. This allows fast and simple manufacturing methods by means of which increased costs for raw materials can possibly be compensated for.

In one method a data record of a dental prosthesis part and the data record of a residual tooth part, which can for instance be stored in a computer, is examined as to whether the dental prosthesis part or a part thereof can be mounted onto the residual tooth portion. This examination, without the examination as to producibility, solves the object according to the invention.

The method may also be to examine a data record as to whether it represents a dental prosthesis with undercuts. If undercuts do not exist, an examination as to mountability may be dispensed with, since a mountability is then always given. A producibility by a 3-axis milling machine is also given in principle, wherein, however, possible limit angles must be taken into consideration between the milling tool and the milled surface.

The computer comprises means for storing a data record and means by means of which the producibility with one or several determined manufacturing methods and/or the mountability can be examined. A computer comprising a means for storing a data record can also be used, which comprises means for examining the data record as to undercuts.

The methods according to claims 1 to 28 are advantageously implemented in software since thereby large amounts of data, as they occur in data records of dental prosthesis parts or residual tooth portions, can well and quickly be processed. The software may be stored on a computer-readable medium.

Embodiments of the present invention shall be explained by means of the enclosed Figures.

Figure 1:
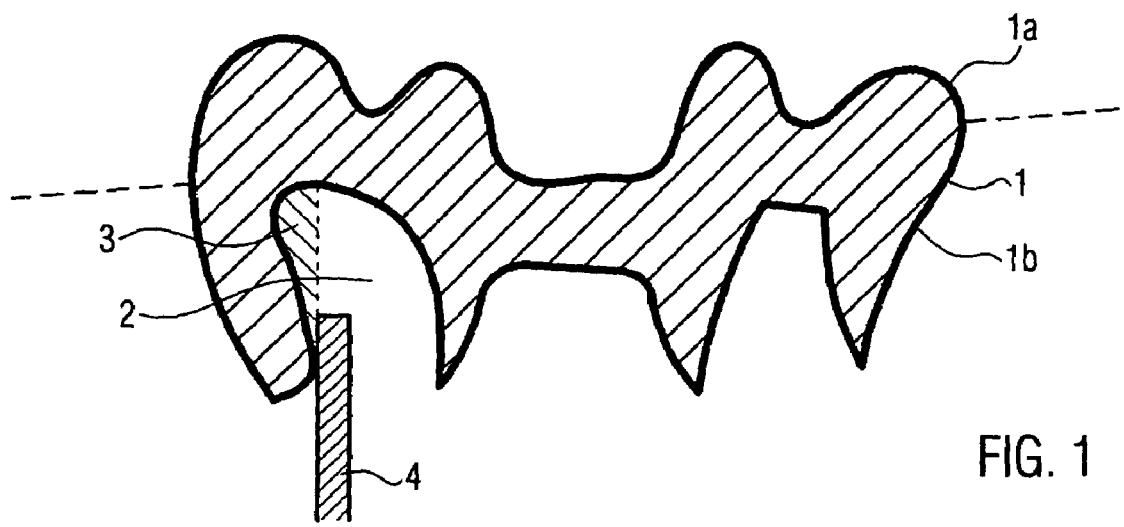
FIG. 1 shows a schematic view of a dental prosthesis part and a milling tool.

In FIG. 1 a dental prosthesis part 1 is shown, which is represented by a data record. The dental prosthesis part 1 has an outer side 1 a and an inner side 1 b. The inner side 1 b is the side facing the residual tooth portion.

The dental prosthesis part, as it is shown in FIG. 1, shall for instance be manufactured by milling. A respective cylindrical milling tool is indicated by reference numeral 4. By this milling tool 4 the cavity 2 of the dental prosthesis part shall be produced. By using a 3-axis milling machine, which may move the cylindrical milling tool 4 linearly in the three spatial directions, the portion 3 of the cavity 3 is only accessible if the shape of the dental prosthesis part 1 would be changed below the portion 3. This is caused by the fact that the portion 3 represents an undercut. The portion of the undercut cannot be achieved by a milling tool 4, as it is shown in FIG. 1, by a 3-axis milling machine. By means of such a milling machine the dental prosthesis part can therefore not be manufactured.

Figure 2:
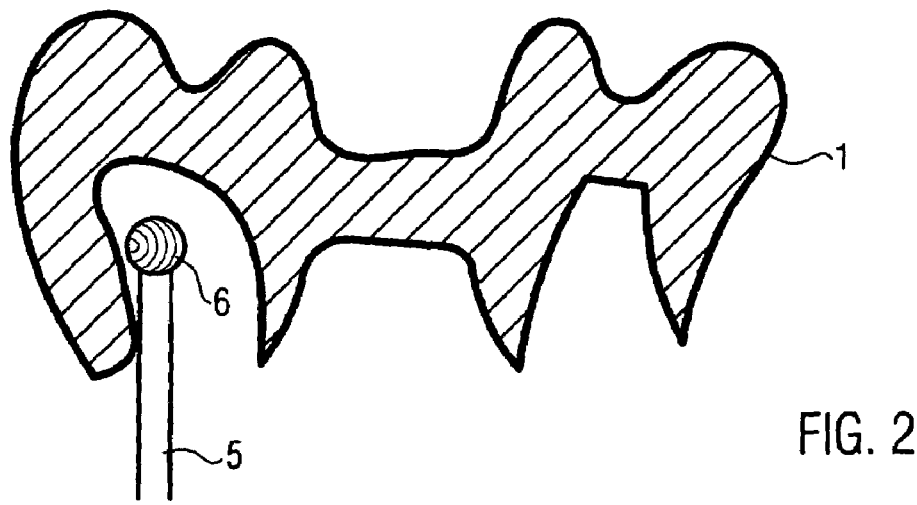
FIG. 2 shows a schematic view of a dental prosthesis part and a different milling tool.

FIG. 2 shows the case in which a shaping tool 5 is used as a milling tool. This tool has a thickening 6 on its upper end. By means of such a milling tool, it is also possible by a 3-axis milling machine to produce small undercuts. In the case as it is shown in FIG. 2, the portion 3 of FIG. 1 does not become fully accessible by such a milling tool.

By tilting the milling tool 4 or 5 by a 4-axis or 5-axis milling machine the portion 3 of FIG. 1 becomes accessible for being milled out, however, milling machines or milling times of this type are significantly more expensive.

In the method according to the invention it can therefore first of all be examined by which manufacturing method a dental prosthesis part can be manufactured. If the examination was carried out for several manufacturing methods, the most cost-effective manufacturing method can be chosen.

In the examination of the producibility, the examination of the inner side 1 b and the outer side 1 a can be carried out separately from one another. It is also possible that only the inner side or only the outer side is examined as to its producibility. This may be sensible, since in the case of a non-producibility of the lower side, other measures will have to be taken compared to a non-producibility of the outer side. In the case of a non-producibility of the outer side, the outer side must only be re-shaped, whereas in the case of a non-producibility of the inner side either the data record of the inner side must be shaped or the residual tooth portion must be processed.

The problem concerning the producibility of a dental prosthesis part, as it is shown in FIG. 1, results from the fact that the dental prosthesis part 1 reveals an undercut 3. Problems concerning producibility can therefore for instance be carried out by examining a data record as to whether it has undercuts.

Figure 3:
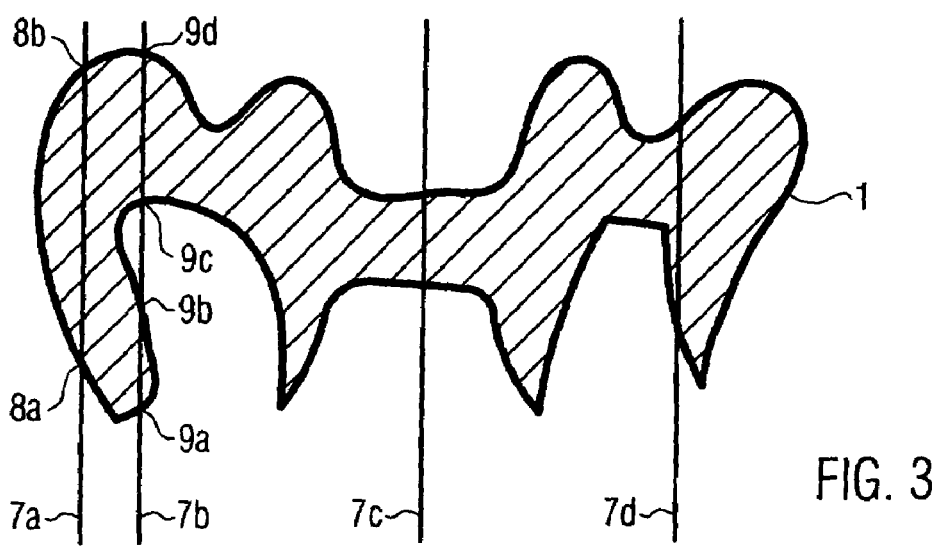
FIG. 3 shows a schematic view of a dental prosthesis part.

FIG. 3 schematically shows such a method. The data record of the dental prosthesis part 1 is in this case cut with different lines 7 a to 7 d. If the outer contour of the data record reveals two intersecting points only with all lines, undercuts do not exist. This can e.g. be seen in line 7 a, which reveals an intersecting point with the contour of the data record at 8 a and at 8 b. The line 7 b, however, comprises four intersecting points, 9 a, 9 b, 9 c, 9 d. This indicates that an undercut is given. In lines 7 c and 7 d, only two intersecting points exist so that undercuts do not exist in this case.

The direction of lines 7 a, 7 b, 7 c, can be varied to examine the data record as to undercuts from other directions. If the lines 7 a to 7 d are e.g. as in FIG. 3 rotated in counter-clockwise direction so that the undercut in the area 3 of the cavity 2 is no longer detected, an undercut in the cavity 2 on the right side results.

Problems with producibility therefore particularly result, if undercuts are detected from all directions. In this case, a producibility with a single milling tool (see reference numeral 4 in FIG. 1) by a 3-axis milling machine is not possible.

Figure 4:
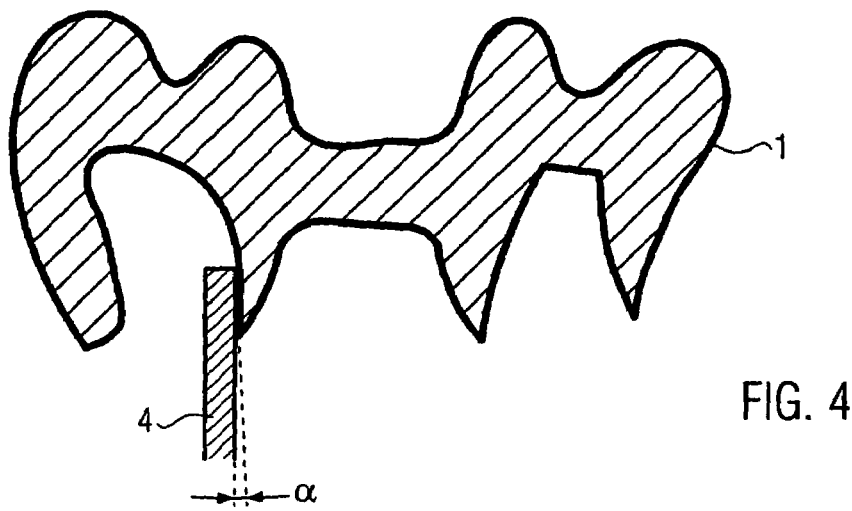
FIG. 4 shows a schematic view of a dental prosthesis part and a milling tool.

Even in the case that the data record of a dental prosthesis part does not reveal undercuts, problems in manufacture may result. This is illustrated in FIG. 4, in which the milling tool 4 is arranged flatly under a very small angle α on the inner side of the dental prosthesis part 1. In the case of such small angles between the milling tool and the milled surface wobbling of the milling tool may easily occur, which then leads to undesired inaccuracies in the manufacture of a dental prosthesis part 1.

The method of examining producibility therefore advantageously considers the limit angle between the milling tool and the milled surface. This may be achieved in the method illustrated in FIG. 3 in that the angle between the straight line and the surface of the dental prosthesis part represented by the data record is determined at the intersecting points.

Figure 5A:
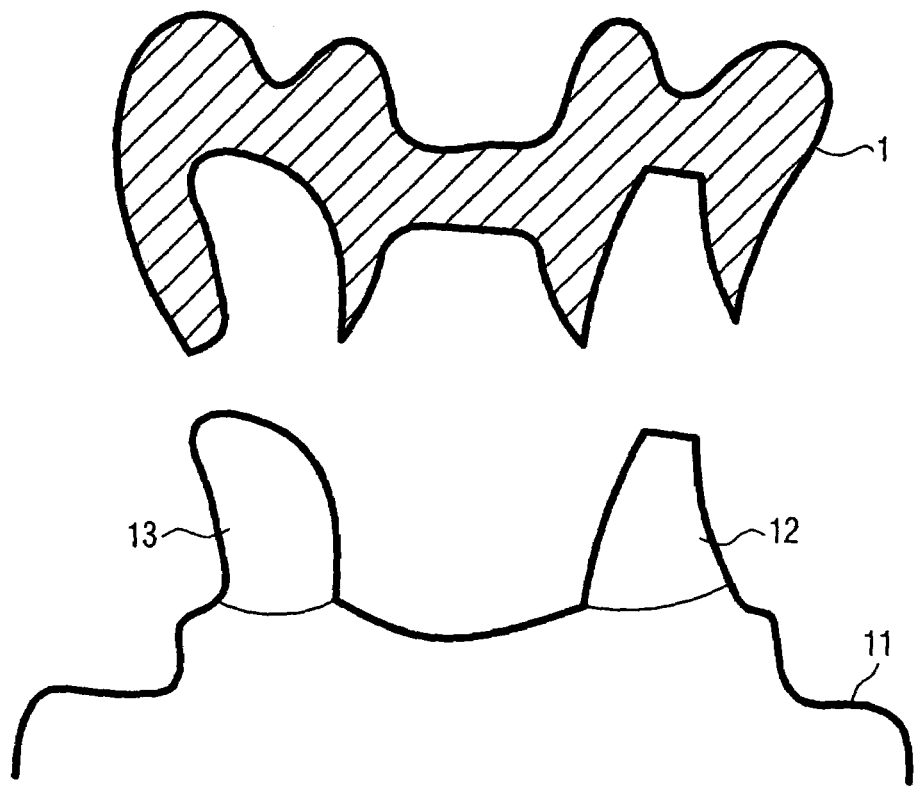
FIG. 5 shows a schematic view of a dental prosthesis part and a residual tooth portion.

FIG. 5 *a* shows the dental prosthesis part 1 together with a residual tooth portion 11. This residual tooth portion 11 comprises two stumps of teeth or implant piles 12, 13. While the dental pile 12 is ground conically, the dental pile 13 is not exactly ground conically.

Figure 5B:
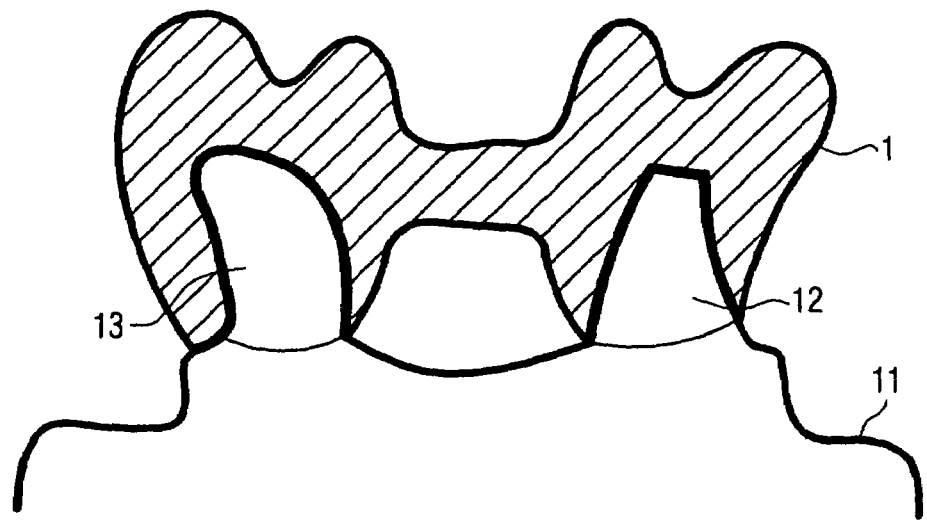

It is shown in FIG. 5 *b* how the dental prosthesis part 1 is mounted onto the residual tooth portion 11. The inner side of the dental prosthesis part 1 is adapted to the shape of the residual tooth portion 11. This particularly applies to the portions of the stumps of the teeth 12, 13. The fact that the dental prosthesis part 1, as shown in FIG. 5*b*, fits onto the residual tooth portion 11 does not mean that the dental prosthesis part 1 can also be mounted onto the residual tooth portion 11. This is illustrated by means of FIG. 6. It is shown how it is attempted to mount the dental prosthesis part from the top linearly onto the residual tooth portion 11. However, a collision in the area 14 between the dental prosthesis part 1 and the stump of tooth 13 occurs. This problem is also traced back to the fact that the dental prosthesis part 1 in the area 3 (see FIG. 1) has an undercut. The dental prosthesis part 1 has this undercut, since the residual tooth portion 11 is not matchingly formed but rather also reveals an undercut.

Figure 6:
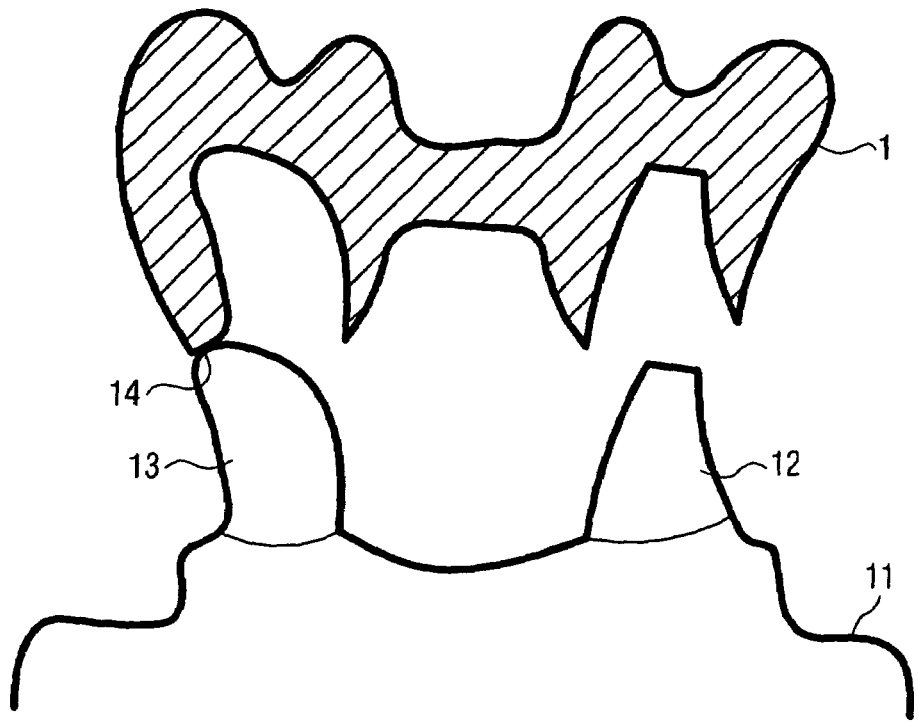
FIG. 6 shows another schematic view of a dental prosthesis part and a residual tooth portion.
Figure 7:
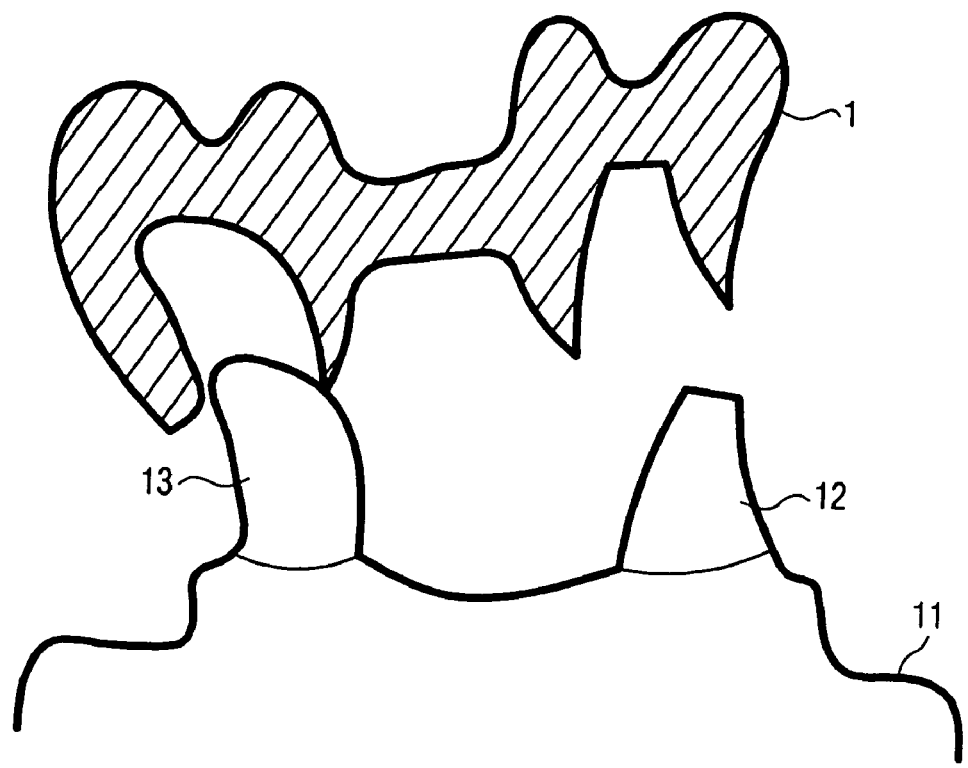
FIG. 7 shows a different view of a dental prosthesis part and a residual tooth portion.
Figure 8:
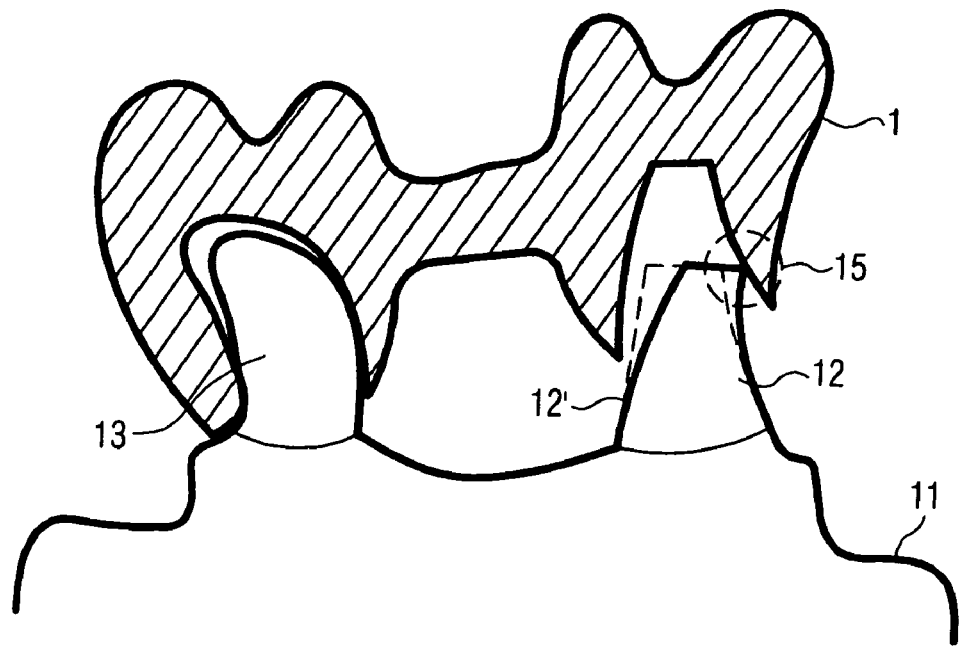
FIG. 8 shows a schematic view of a dental prosthesis part and a residual tooth portion during mounting or removal.

Before manufacture of a dental prosthesis part 1, the mountability can therefore be examined by means of the data record. In this connection the data record of the dental prosthesis part 1 and the residual tooth portion 11 is simulated in different positions relative to one another. This is shown in FIGS. 6, 7 and 8. In this connection the data records are preferably translated against one another as well as rotated against one another. Rotating data records are e.g. shown in FIG. 7. While a linear mounting, as it is shown in FIG. 6, is not possible, a rotation can still be possible, as it is shown in FIG. 7. A precise examination of the data records of the example of FIGS. 6, 7 and 8 it reveals that in the case of a rotation, which enables the mounting of the dental prosthesis part 1 onto the stump of the tooth 13, a problem may occur in the area 15 at the stump of the tooth 12. The dental prosthesis part 1 and the stump of the tooth 12 contact one another so that a mounting may not easily be possible.

It is shown in FIG. 8 show the stump of tooth 12 can be rotated to a position 12' due to its inherent movement. By a slight movement of the stump of tooth 12, the dental prosthesis part 1 can then be mounted by exerting the respective force while being mounted onto the residual tooth portion 11. With the dental prosthesis part being mounted, the stump of tooth 12 shall be back in its original position, since otherwise enduring pain may occur.

In the method of examining the mountability it is therefore advantageous to take into consideration an inherent movability of teeth. They may for instance be stored in the form of tilt angles for different teeth in tables. Molars in this connection have a different inherent movability compared to incisors. An age-dependency of the patient or other criteria can be used for the consideration of the inherent movability. A linear inherent movability can also be taken into consideration, i.e. not only a tilting to the teeth.

Furthermore, it may be taken into consideration that implant piles do not reveal any inherent movability. When examining the mountability it is advantageous to determine whether the inherent movability of the teeth must be taken into consideration or not and if this is the case to which extent the inherent movability is required to later mount a dental prosthesis part. This allows the user to determine whether the required inherent movability is acceptable.

When examining the mountability, it can either be started out from a state, as it is shown in FIG. 5 *a* and it can be attempted by simulation of the relative position of the data records to one another to reach the state in FIG. 5 *b*, or vice versa it can be started out from the relative position, as it is shown in FIG. 5*b* and it may be attempted to simulate to reach the state as it is shown in FIG. 5 *a*.

Figure 9:
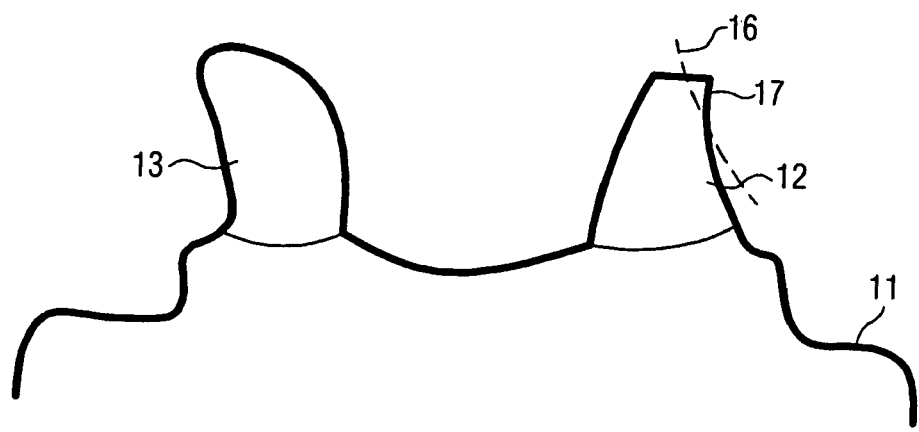
FIG. 9 shows a schematic view of a preparation instruction.

If it results in the examination of mountability (possibly also in consideration of the inherent movability of teeth) that a mountability is not given, the possibility exists to modify the residual tooth portion. For this purpose, a respective preparation instruction may be generated, as is schematically shown in FIG. 9. It is shown there that the portion 17 of the stump of tooth 12 is to be removed by means of grinding. For visualization, a separation line or the like may for instance be shown or that portion of the stump of the tooth that is to be removed may be colored or marked in any manner. In this connection both two-dimensional as well as three-dimensional illustrations may be used. A respective preparation instruction may then be sent to a dentist or the like to modify the respective residual tooth portion.

Figure 10:
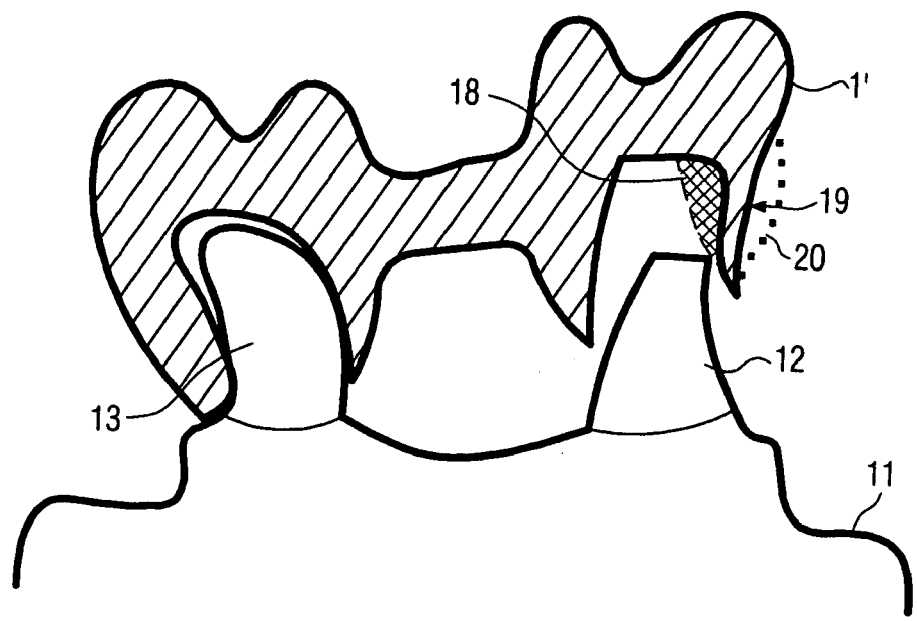
FIG. 10 shows a schematic view of a corrected dental prosthesis part and a residual tooth portion.

The other possibility is to modify the data record already before manufacture so that a mountability is given. This is schematically shown in FIG. 10. The dental prosthesis part 1' in FIG. 10 differs from the dental prosthesis part 1 in the remaining Figures in that in the cavity, which belongs to the stump of the teeth 12, a portion 18 is removed on the right side. Thereby a collision in the area 15, as it is shown in FIG. 8 in the rotation process, is avoided, so that a dental prosthesis part 1' can easily be mounted due to a modified data record.

As may be seen in FIG. 10, a problem may occur with the required material strength in the area 19. Caused by a thinning of the dental prosthesis part on its right portion by removing the portion 18, the material strength in the area 19 becomes so thin that the dental prosthesis part possibly becomes too fragile. In the modification of the data record for the dental prosthesis part 1', the required material strength can e.g. be taken into consideration. In the area 19 the material strength can be slightly increased on the outer side, as is indicated by line 20.

A particularly preferred embodiment of the method shall now be described. In this connection only the part of the data record that corresponds to the inner side 1 *b* is produced or evaluated. Only the part of the inner side can be observed that shall come into contact with the residual tooth portion or the stumps. Only this portion is examined as to undercuts and/or its producibility and/or its mountability. Only the inner side or a part thereof is problematic in the mountability so that the examination of the inner side is sufficient for the examination of mountability. Depending on the result of the examination, either the residual tooth portion or the data record of the dental prosthesis part may be modified, as described above.

Figure 11:
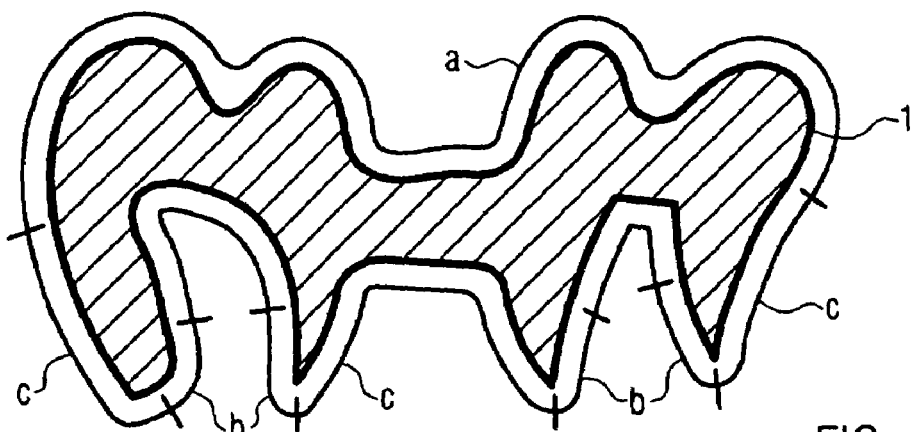
FIG. 11 shows a schematic view of zones of a dental prosthesis to be processed differently.

Only after defining the inner side of the dental prosthesis part, after examining the producibility and the mountability is the part of the data record, which represents the outer side of the dental part or the missing part of the data record shaped automatically. The required wall thickness may then be taken into consideration in consideration of the desired material of the dental prosthesis part, the manufacturing costs, manufacturing time etc. It is also possible to take into consideration individual definitions for the outer dimensions for the modification of generation of the data record according to the outer side. These dimensions may for instance be given by adjoining teeth between which the dental prosthesis part must be fitted In FIG. 11 different zones a, b and c are marked on the surface of the dental prosthesis part 1. The different zones define zones for which different manufacturing modes can be used. That means that e.g. in the milling process different feed speeds of the milling head or different speeds of the milling tool may be used. Higher feed speeds may lead to a slightly rougher surface, which, however, can be accepted on the outer side or in the zone a. At higher feed speeds, the manufacturing times can be shortened. In the same manner, other manufacturing parameters for an optimized manufacturing speed or minimized manufacturing costs for the different zones may be selected. In the area c it can be operated at a mean precision, since here a favourable accuracy is responsible for a favourable seat. In area b (preparation limit) a possibly high precision is required, since this portion seals the connection between the dental prosthesis part and the stump of the tooth. If gaps exist, depositions or caries may occur, which is not desired. The generation of the parameters for the different zones a, b and c can be carried out fully automatically or by the assistance of an operator.

Figure 12:
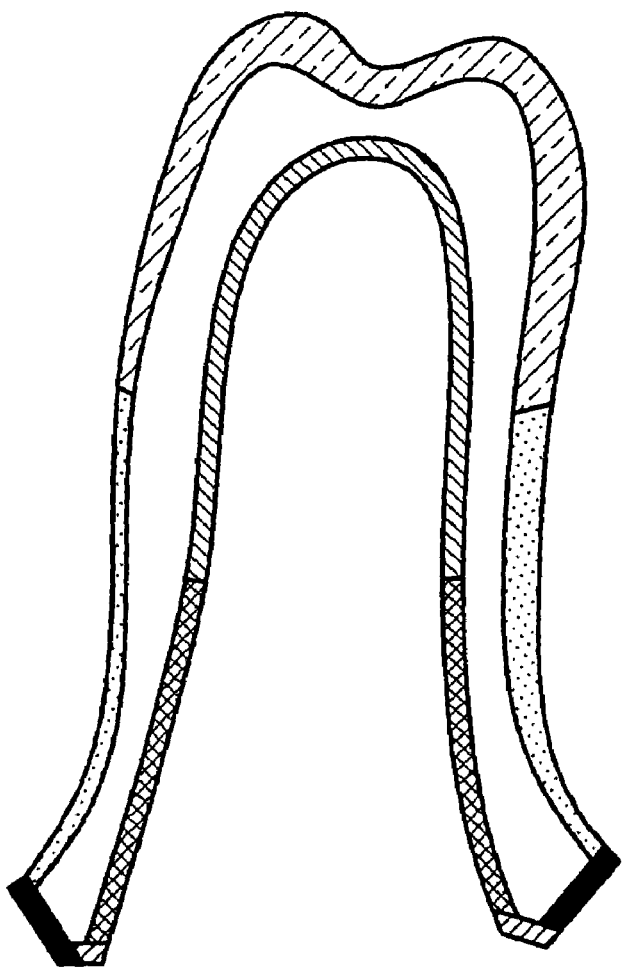
FIG. 12 shows a different schematic view of zones of a dental prosthesis part to be processed differently.

FIG. 12 shows another cut through a data record of a dental prosthesis part 1. In this case different portions of the surface are provided with different hatchings, which as the zones a, b and c in FIG. 11 point to different parameters in the manufacture. Particularly at the preparation limit a high precision is required, which can be achieved with the respective parameters during manufacture.

Figure 13:
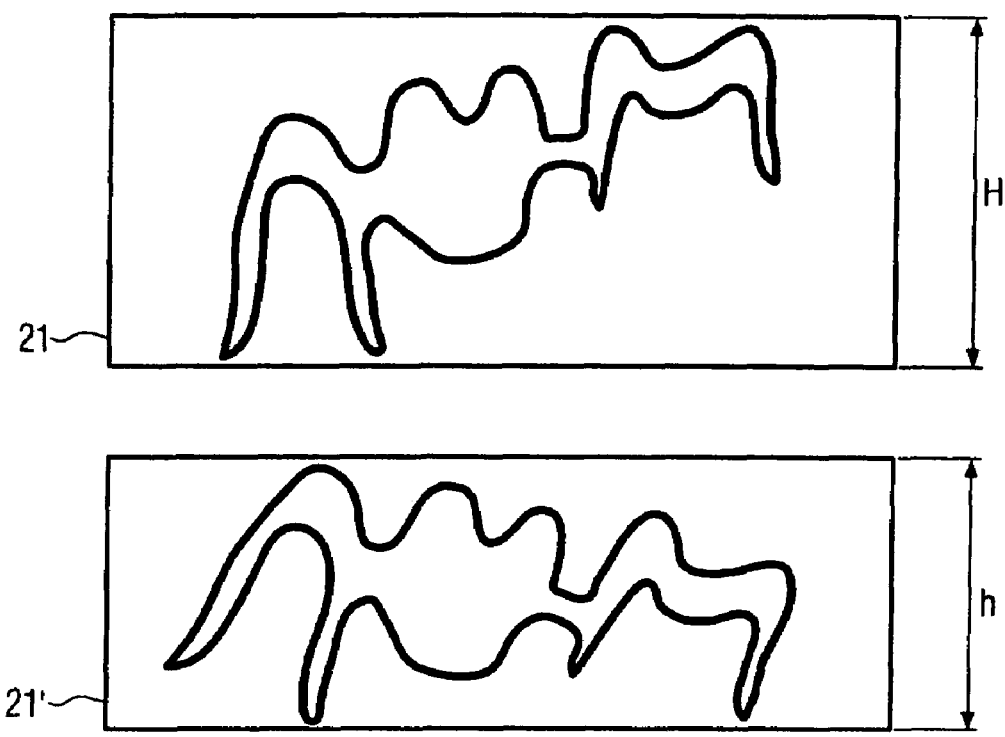
FIG. 13 shows a schematic view of a data record in different orientations relative to a blank.

FIG. 13 shows a data record of a dental prosthesis part in different orientations relative to a blank 21 or 21', respectively. In the upper orientation the dental prosthesis part is practically undercut-free with respect to the direction of the height H of the blank, however, it requires a blank with the large height H. The undercut freedom allows cost-effective manufacturing methods, however, it requires a more expensive blank. Although the lower orientation allows lower blank costs, since the required height h is smaller than H, however, it requires more laborious and thus cost-intensive manufacturing methods, since with a simple 3-axis milling machine the undercuts cannot be manufactured or at most by using special shaping tools. Thus, it is sensible to determine the minimum height h, which is required to produce a dental prosthesis part with a possibly laborious manufacturing method. It is also sensible to determine the smallest height H by means of which the dental prosthesis part can be manufactured by using a simple 3-axis milling machine, i.e. the height at which the dental prosthesis part is oriented in an undercut-free manner. An even larger height of the blank may also be advantageous so that the dental prosthesis part can be oriented in a manner that all milling surfaces are oriented at an angle with respect to the feed direction of the milling tool so that parallel surfaces do not exist that could lead to wobbling of the milling tool. After detecting the different heights the most cost-effective manufacturing method and thus also the required blank height can be determined on the basis of the cost estimation by using stored data.

Figure 14:
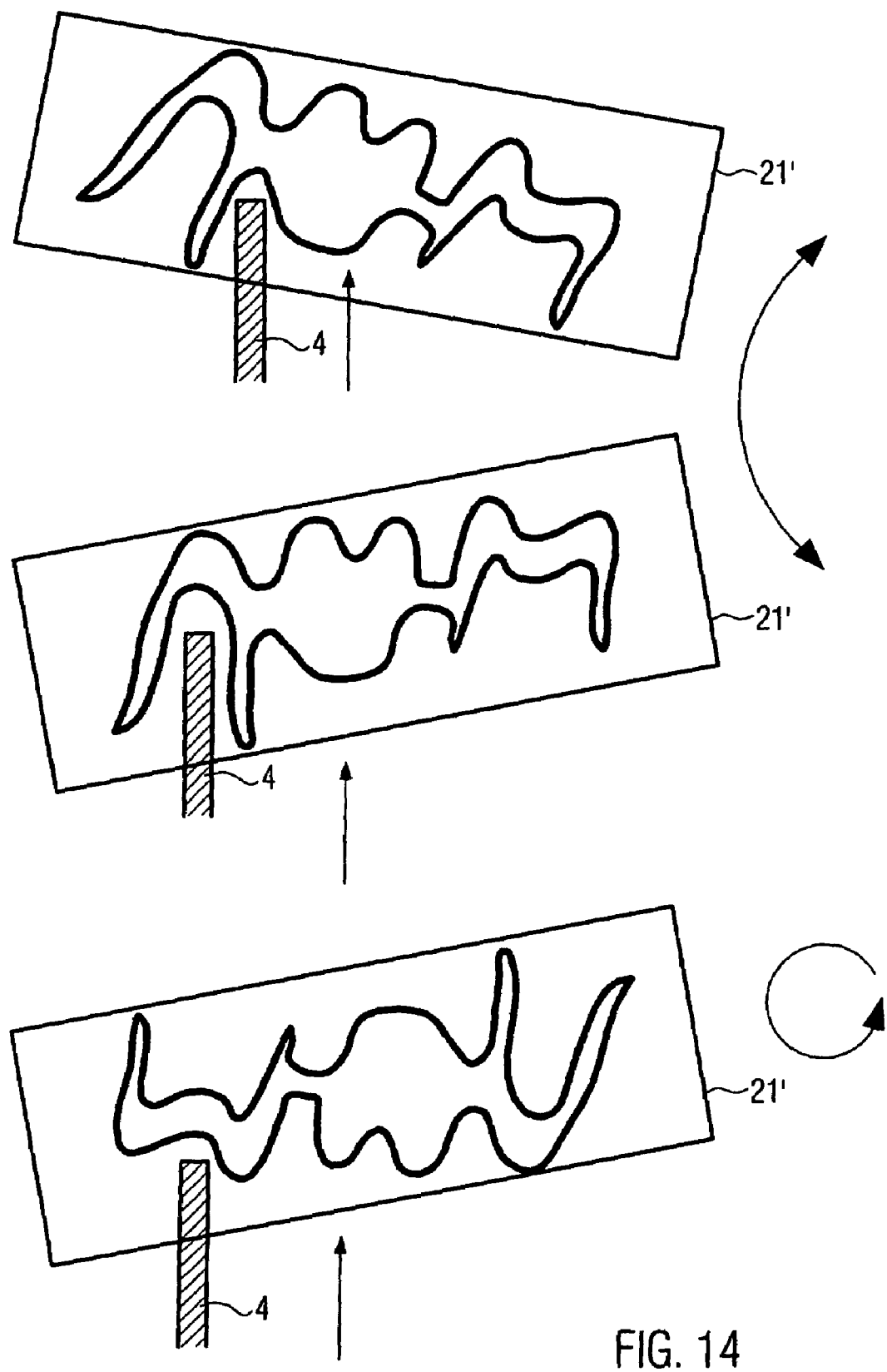
FIG. 14 shows a schematic view of the 3+1-axis milling method.

FIG. 14 describes a manufacturing method using the 3+1-axis milling technology which in some cases may be cost-effective.

In FIG. 14 bottom, the outer side of the dental prosthesis part with a transversely clamped blank 21' is first of all milled. This may take place in one working cycle, since the outer side is oriented in an undercut-free manner. Then the blank is turned (see circular arrow). Then, a part of the inner side of the dental prosthesis part is milled in a first orientation of the blank 21' and subsequently the blank is changed in its orientation (see pivot arrow). The blank may for this purpose be clamped in a different orientation (thus "3+1" technology) without this automatically being carried out by the milling machine. In this second orientation of the blank 21' the rest of the inner side is milled.

The designation "3+1"-axis milling machine therefore designates a machine in which by using a 3-axis milling machine a processing of the blank from different directions is possible, since either the blank and/or the milling head can be arranged in different orientations.

By this technique it is possible using a cost-effective 3-axis milling machine, to obtain the dental prosthesis part from a blank having a minimal height.

The above described different methods, the method for examination producibility, mountability and undercuts can all be carried out individually. They can also be carried out in any combination in series.

In the automatic manufacture of dental prosthesis parts it is common that a dental technician generates a data record for a dental prosthesis part and transmits same to a manufacturing center in which a dental prosthesis part is manufactured by means of this data record.

The methods described here may be carried out by a dental technician as well as in the manufacturing center.

The examination of the mountability and the producibility at the dental technician may be used to estimate the manufacturing time and manufacturing costs already when producing the data record by a dental technician.

When carrying out the method in a manufacturing center, the result of the examination of producibility may for instance be used to select a cost-effective manufacturing method.

The invention claimed is:

1. A method, embodied on a computer-readable medium and executed on a processor having memory means, comprising:

examining a first data record representing a shape of a dental prosthesis element; categorizing the shape of the dental prosthesis element according to predetermined manufacturing parameters, based on results of the examination;

determining whether the dental prosthesis element can be manufactured by at least one predetermined manufacturing method;

classifying the first data record based on the determination for at least one of later manufacturing considerations, later shaping considerations, and later mounting considerations;

examining a second data record representing a shape of a residual tooth portion assogated with the dental prosthesis element;

categorizing the shape of the dental prosthesis element according to predetermined mountability parameters, based on results of the examination of the first data record and the examination of the second data record; and determining whether the dental prosthesis element can be mounted on the residual tooth portion;

wherein the dental prosthesis element is one of a dental prosthesis, a dental prosthesis part, and a part thereof; and wherein the mountability parameters relate to whether the dental prosthesis element can be mounted onto the residual tooth portion.

2. A method as claimed in claim 1, wherein the first data record includes a first part corresponding to an inner side of the dental prosthesis element, and a second part corresponding to an outer side of the dental prosthesis element; and examining the first data record includes examining only one of the first part and the second part of the first data record in order to make the determination with respect to the respective one of the inner side and the outer side of the dental prosthesis element.

3. A method as claimed in claim 2, wherein only one of the first part and the second part of the first data record is examined, and categorizing the shape of the dental prosthesis element includes characterization as to whether one or more undercuts exist in said one of the first part and the second part of the dental prosthesis element.

4. A method as claimed in claim 1, characterized in that the predetermined manufacturing methods comprise at least one of:
   milling by at least one of a 3-axis milling machine, a 3+1-axis milling machine, a 4-axis milling machine, and a 5-axis milling machine, and
   milling by at least one of a 3-axis milling machine, a 3+1axis milling machine, a 4-axis milling machine, and a 5-axis milling machine using a shaping tooth, and
   laser sintering.

5. A method as claimed in claim 1, wherein categorizing the shape of the dental prosthesis element includes characterization as to whether one or more undercuts exist in the dental prosthesis element.

6. A method as claimed in claim 1, wherein determining whether the dental prosthesis element can be manufactured by at least one predetermined manufacturing method includes considering a limit angle, wherein the limit angle represents a minimum value for an angle disposed between a milling tool and a milled surface of the dental prosthesis element during at least one of manufacture and shaping of the dental prosthesis element.

7. A method as claimed in claim 6, wherein determining whether the dental prosthesis element can be manufactured by at least one predetermined manufacturing method includes determining the minimum value of the limit angle and providing a value of the limit angle to a user.

8. A method as claimed in claim 1, further comprising, after determining whether the dental prosthesis element can be manufactured by at least one predetermined manufacturing method, carrying out part of a manufacturing method, during which predetermined information is used.

9. A method as claimed in claim 8, further comprising:
   selecting a manufacturing type of the at least one predetermined manufacturing method based on the determination; and
   using a computer to generate an indication of the selection.

10. A method as claimed in claim 9, wherein the indication is generated as one of a print-out, a screen display, a drawing-up, or a modification of an entry in a database.

11. A method as claimed in claim 10, wherein the indication is generated as modification of an entry in a production database.

12. A method as claimed in claim 8, wherein the predetermined information includes at least one of manufacturing duration, manufacturing costs, and material costs.

13. A method as claimed in claim 1, wherein the mountability parameters include at least one of linear mounting considerations, linear removal considerations, pivoting-on considerations, and pivoting away considerations.

14. A method as claimed in claim 13, further comprising simulating at least one of relative linear shifts of the first and second data records and relative rotational movements of the first and second data records.

15. A method as claimed in claim 13, wherein, if at least one of
   it is determined that the dental prosthesis element cannot be manufactured by any of the at least one manufacturing method and
   it is determined that the dental prosthesis element cannot be mounted on the residual tooth portion,
   then the method further comprises generating a preparation instruction that indicates how a shape of the residual tooth portion can be modified to result in at least one of a positive determination with respect to manufacturing and a positive determination with respect to mounting.

16. A method as claimed in claim 15, wherein generating the preparation instruction includes at least one of
   preparing the preparation instruction in the form of at least one of text and at least one image; and
   transmitting the preparation instruction by means of electronic data transmission.

17. A method as claimed in claim 16, wherein the preparation instruction is generated as one of a screen display and a print-out.

18. A method as claimed in claim 16, further comprising transmitting the preparation instruction to at least one of a dentist and a dental technician.

19. A method as claimed in claim 13, wherein
   if it is determined that the dental prosthesis element cannot be manufactured by any of the at least one manufacturing method, and
   if it is determined that the dental prosthesis element cannot be mounted on the residual tooth portion,
   then the method further comprises:
   modifying the data record of the dental prosthesis element; and
   repeating the method until at least one of the following is determined;
   the dental prosthesis element can be manufactured by at least one of the at least one manufacturing method; and
   the dental prosthesis element can be mounted on the residual tooth portion.

20. A method as claimed in claim 19, wherein modifying the data record of the dental prosthesis element includes considering at least one criterion selected from the group of criteria consisting of:
   sufficient material strength;
   complete inclusion of the stump of the tooth;
   possibly complete contact between the residual tooth portion and the dental prosthesis element;
   manufacturing costs;
   manufacturing time;
   possible manufacturing methods; and
   definitions for outer dimensions of the dental prosthesis element.

21. A method as claimed in claim 1, further comprising generating parameters concerning the manufacturing process based on the first data record.

22. A method as claimed in claim 21, wherein the parameters include an infeed speed of a milling head, a speed of a milling tool, a type of milling tool, and a coolant to be used.

23. A method as claimed in claim 21, further comprising at least one of:
   storing the parameters; and
   providing the parameters to at least one of an output device and an output medium.

24. A method as claimed in claim 1, further comprising determining a minimum height of a blank to be used for milling-out the dental prosthesis element according to at least one of the first data record and an undercut-free orientation of the dental prosthesis element.

25. A method as claimed in claim 1, further comprising rotating the first data record with respect to a system of coordinates of one of a blank and a milling machine so that at least one of a height of the one of the blank and the milling machine is minimized and undercuts are avoided.

26. A method as claimed in claim 1, wherein determining whether the dental prosthesis element can be mounted on the residual tooth portion includes considering inherent movement of the residual tooth portion.

27. A method as claimed in claim 26, wherein the second data record is assembled by one of data input and automatic detection, the method further comprising assogating inherent movability information based on pre-input data with respect to dental movabilities with the residual tooth portion.

28. A method as claimed in claim 26, wherein:
the residual tooth portion is an implant pile; and
the inherent movement is considered to be zero.

29. A method, embodied on a computer-readable medium and executed on a processor having memory means, comprising:
examining a data record representing a shape of a dental prosthesis element;
categorizing the shape of the dental prosthesis element according to predetermined manufacturing parameters, based on results of the examination;
determining whether the dental prosthesis element can be manufactured by at least one predetermined manufacturing method; and
classifying the data record based on the determination for at least one of later manufacturing considerations, later shaping considerations, and later mounting considerations;
wherein the dental prosthesis element is one of a dental prosthesis, a dental prosthesis part, and
a part thereof; and
wherein the data record includes a first part corresponding to an inner side of the dental prosthesis element, wherein at least one of:
categorizing the shape of the dental prosthesis element includes characterization as to whether at least one undercut exists in the dental prosthesis element, based on examination of only the first part of the data record,
determining whether the dental prosthesis element can be manufactured by at least one predetermined manufacturing method includes making the determination based on examination of only the first part of the data record, and wherein the predetermined manufacturing methods include at least one of milling by a 3-axis milling machine, milling by 3+1-axis milling machine, milling by 4-axis milling machine, milling by 5-axis milling machine, milling using a shaping tool, and milling by laser sintering, and
classifying the data record includes making a classification for mounting considerations regarding whether the dental prosthesis element can be mounted on a residual tooth portion, based on examination of only the first part of the data record.

30. A method as claimed in claim 29, further comprising modifying the first part of the data record based on the determination.

31. A method as claimed in claim 29, further comprising, after classifying the data record, shaping an outer side of the dental prosthesis element using at least one of a manual process and an automatic process, taking into consideration at least one of:
wall thickness of the dental prosthesis element;
material of the dental prosthesis element;
manufacturing costs;
manufacturing time;
possible manufacturing methods; and
definitions for outer dimensions of the dental prosthesis element.

32. A method as claimed in claim 29, further comprising selecting the data record from among data records that include a representation of a residual tooth portion.

33. A method as claimed in claim 32, further comprising obtaining the data record of the residual tooth portion by scanning a model.

34. A method as claimed in claim 33, wherein the model is a gypsum model.

35. A method as claimed in claim 29, wherein determining whether the dental prosthesis element can be manufactured by at least one predetermined manufacturing method includes considering a limit angle, wherein the limit angle represents a minimum value for an angle disposed between a milling tool and a milled surface of the dental prosthesis element during at least one of manufacture and shaping of the dental prosthesis element.

36. A method as claimed in claim 35, wherein determining whether the dental prosthesis element can be manufactured by at least one predetermined manufacturing method includes determining the minimum value of the limit angle and providing a value of the limit angle to a user.

37. A method as claimed in claim 29, further comprising, after determining whether the dental prosthesis element can be manufactured by at least one predetermined manufacturing method, carrying out part of a manufacturing method, during which predetermined information is used.

38. A method as claimed in claim 37, wherein the predetermined information includes at least one of manufacturing duration, manufacturing costs, and material costs.

* * * * *